United States Patent [19]
Ogawa et al.

[11] Patent Number: 5,520,177
[45] Date of Patent: May 28, 1996

[54] OXIMETER PROBE

[75] Inventors: Keikitsu Ogawa; Hideo Ozawa; Seishi Matsuno, all of Tokyo, Japan

[73] Assignee: Nihon Kohden Corporation, Tokyo, Japan

[21] Appl. No.: 217,872

[22] Filed: Mar. 25, 1994

[30] Foreign Application Priority Data

Mar. 26, 1993 [JP] Japan .................................. 5-067911

[51] Int. Cl.⁶ ..................................................... A61B 5/00
[52] U.S. Cl. ..................................................... 128/633
[58] Field of Search .......................... 128/633–4, 664–7; 356/39–41

[56] References Cited

U.S. PATENT DOCUMENTS

| | | | |
|---|---|---|---|
| 4,825,879 | 5/1989 | Tan et al. ........................ | 128/677 X |
| 4,865,038 | 9/1989 | Rich et al. ........................ | 128/633 |
| 4,964,408 | 10/1990 | Hink et al. ....................... | 128/633 |
| 5,094,240 | 3/1992 | Muz ................................. | 128/633 |
| 5,217,012 | 6/1993 | Young et al. ...................... | 128/633 |
| 5,237,994 | 8/1993 | Goldberger ....................... | 128/633 |

*Primary Examiner*—Angela D. Sykes
*Attorney, Agent, or Firm*—Sughrue, Mion, Zinn, Macpeak & Seas

[57] ABSTRACT

An oximeter probe to be wound on a fingertip of an object and used to measure the oxygen saturation of blood is completely shielded from electrical noises. The front face of an a flexible printed circuit board on which an a light-emitting device and a photodetective are mounted is covered by a conductive sheet having windows at the locations which correspond to the LED and the photodetector. The back face of the circuit board is covered by shield copper foil.

9 Claims, 1 Drawing Sheet

OXIMETER PROBE

BACKGROUND OF THE INVENTION

1. Field of Invention

This invention relates to an oximeter probe which is attached to a part of an object such as a fingertip and in which light emitted from a light emitting portion and passed through living tissue of the object is received by a light receiving portion, so that the pulse wave of blood flowing through a blood vessel is detected and the oxygen saturation of blood is measured.

2. Related Art

In such an oximeter probe, conventionally, an LED functioning as the light emitting portion, and a photodetector (hereinafter, as "PD" when applicable) functioning as the light receiving portion are mounted on a flexible printed circuit board (hereinafter, as "FP board" when applicable), the FP board is wound on a fingertip, and a light shielding tape is wound on the outer periphery. Under this state, the oxygen saturation is measured.

In the prior art oximeter probe, optical noises such as external light are prevented from entering the PD by winding the FP board with the light shielding tape, but no countermeasure against electrical noises is taken. Accordingly, there arises a problem in that electrical noises from the outside enter the FP board, particularly the PD to produce an error in measuring results.

SUMMARY OF THE INVENTION

The invention has been made in view of the above-mentioned circumstances. It is an object of the invention to provide an oximeter probe which can be shielded completely from electrical noises.

In order to attain this and other objects, in an oximeter probe comprising an FP board on which an LED and a PD are mounted and which is to be attached to a part of an object such as a fingertip to measure an oxygen saturation of blood, the oximeter probe further comprises: a conductive sheet covering the face of the FP board on which the LED and the PD are mounted, windows being respectively formed at locations corresponding to the LED and the PD, and shield copper foil covering the back face of the FP board; and a conductive and transparent shield sheet, when the windows are large, covering at least one of the paired windows which corresponds to the PD.

According to the above-mentioned configuration, both faces of the FP board are covered by the conductive sheet and the shield copper foil, and, when the windows formed in the conductive sheet are large, the windows are covered by the conductive and transparent shield sheet. Therefore, it is possible to prevent external electrical noises from entering the FP board, particularly the PD, whereby the probe can be shielded entirely from external electrical noises.

DETAILED DESCRIPTION OF THE PREFERRED EMBODIMENTS

Hereinafter, preferred embodiments of the oximeter probe according to the invention will be described with reference to the drawings.

Figure 1:
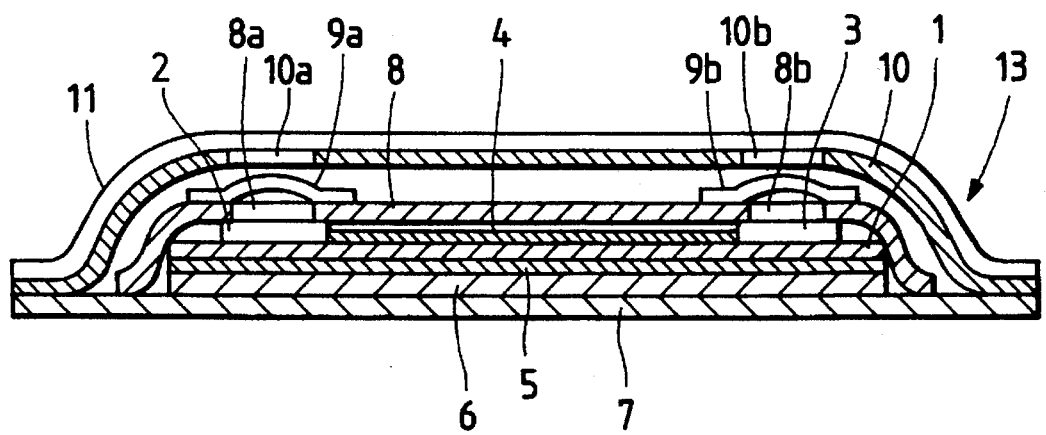
FIG. 1 is a section view showing a configuration of an embodiment of the oximeter probe of the present invention.
Figure 2:
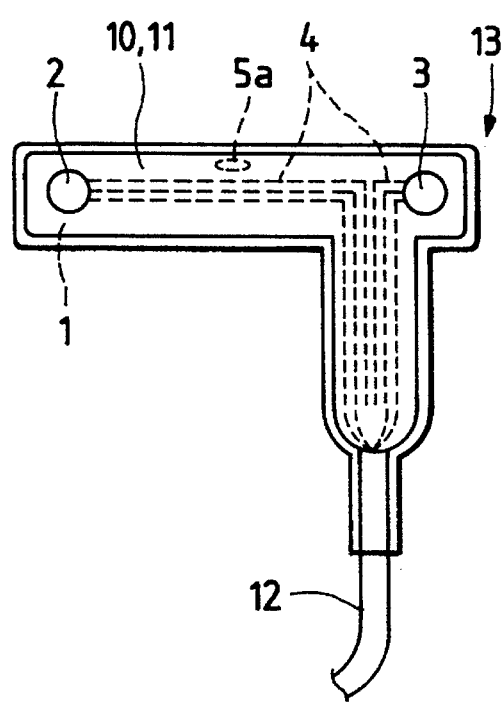
FIG. 2 is a plan view of the probe of the present invention as shown in FIG. 1.

FIGS. 1 and 2 show a configuration of an embodiment of the invention. In FIGS. 1 and 2, an FP board 1 has a substantially T-like shape in a plan view, and an LED 2 and a PD 3 are mounted in the vicinity of the ends of the one leg of the FP board 1, respectively. On the second leg of the FP board 1, which is perpendicular to the one leg, are formed wiring patterns 4. These wiring patterns 4 supply electric power to the LED 2 from an external source and output a signal detected by the PD 3. Mesh-like shield copper foil 5 is formed integrally with the face of the FP board 1 that lies opposite to the side on which the LED 2 and the PD 3 are mounted. A heat sink plate 6 which is made of silicone rubber is adhered to the outer face of the shield copper foil 5. A vinyl sheet 7 is adhered to the outer face of the heat sink plate 6 in such a manner that the vinyl sheet 7 protrudes from the outer periphery of the heat sink plate 6.

On the other hand, the face of the FP board on which the LED 2 and the PD 3 are mounted is covered by a flexible conductive sheet 8. The whole of the outer periphery of the conductive sheet 8 is adhered to the vinyl sheet 7. Windows 8a and 8b are formed at the locations of the conductive sheet 8 which correspond to the LED 2 and the PD 3, respectively. The windows 8a and 8b are covered by shield sheets 9a and 9b which have an Ag-deposited inner face and which are electrically conductive and optically transparent. A terminal portion 5a (not shown in FIG. 1) which is separated from the wiring patterns 4 and grounded is disposed on the side of the FP board 1 on which the LED 2 and the PD 3 are mounted. The terminal portion 5a is electrically connected with the shield copper foil 5 via a through hole which passes through the FP board 1. Furthermore, a part of the conductive sheet 8 contacts with the terminal portion 5a to be electrically connected therewith.

The upper faces of the conductive sheet 8 and the shield sheets 9a and 9b are covered by a vinyl sheet 10 which is made of the same material as that of the vinyl sheet 7 covering the back face of the FP board 1, so that the combination of the vinyl sheets 7 and 10 covers the whole portion of the front and back faces of the T-like FP board 1. The outer peripheries of the vinyl sheets 7 and 10 are adhered to each other. Openings 10a and 10b are formed at the locations of the vinyl sheet 10 which correspond to the LED 2 and the PD 3, respectively. A transparent sheet 11 is adhered to the surface of the vinyl sheet 10 so as to cover the openings 10a and 10b. One end of each of the wiring patterns 4 formed on the FP board 1 is connected at one end portion of the second leg of the FP board 1 with the main unit of the oximeter through lead wires 12. One end of the conductive sheet 8 and that of the shield copper foil 5 are electrically connected with each other at the terminal portion 5a of the FP board 1, and connected with the main unit of the oximeter through lead wires 12 to be grounded.

Figure 3:
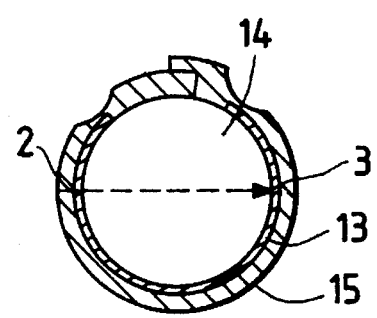
FIG. 3 is a section view showing a state in which the probe of FIG. 2 is wound on a finger.

Next, the operation and effect attained when the oximeter probe 13 of the embodiment is attached to a finger will be described with reference to FIGS. 1 to 3. As shown in FIG. 3, the probe 13 is wound on a finger 14 in such a manner that the LED 2 and the PD 3 oppose to each other, and an adhesive tape 15 is wound on the outside so that the probe is closely contacted and fixed to the finger 14. Since the probe 13 is covered by the vinyl sheets 7 and 10 and the openings 10a and 10b are closely contacted to the finger 14, external disturbance light is prevented from entering the inside of the probe 13. Light emitted from the LED 2 passes through the tissue of the finger 14 to be received by the PD 3, whereby the pulse wave of blood flowing through a blood vessel in the tissue can be detected to measure the oxygen saturation. Even when electrical noises are radiated from ambient sources to the probe 13, electrical noises are prevented from entering the probe 13, and particularly from entering the PD 3. This is so because both faces of the FP board are covered, by the shield copper foil 5 on the one hand and by the conductive sheet 8 on the other, and the windows 8a and 8b of the conductive sheet 8 are covered by the shield sheets 9a and 9b which are transparent and conductive. Consequently, the oxygen saturation can be measured more accurately when using the probe 13 than was possible with prior art devices.

In the above, an embodiment in which the windows 8a and 8b formed in the conductive sheet 8 are respectively covered by the shield sheets 9a and 9b has been described. Alternatively, the shield sheet 9a for the LED 2 which is not liable to be affected by electrical noises may be omitted. Furthermore, in the case where the windows 8a and 8b can be reduced to a sufficiently small size at which neither the LED nor the PD is affected by electrical noises, both the shield sheets 9a or 9b may be omitted. When the windows 8a and 8b of the conductive sheet 8 are formed as a mesh, or the conductive sheet 8 itself is formed as one body by a conductive member which is optically transparent, the configuration can be further simplified.

As described above, according to the oximeter probe of the invention, since both faces of a flexible printed circuit board on which a light emitting portion and a light receiving portion are mounted are covered by a conductive sheet and shield copper foil, the probe can be shielded completely from external electrical noises and the oxygen saturation can be measured correctly.

What is claimed is:

1. An oximeter probe comprising:
    a flexible printed circuit board having a front face on which a light emitting member and a light receiving member are mounted and having a back face, said flexible printed circuit board being configured to be attached to a part of an object to measure an oxygen saturation of blood;
    a conductive sheet covering the front face of said flexible printed circuit board on which the light emitting member and the light receiving member are mounted, said conductive sheet having windows formed at locations corresponding to the light emitting member and the light receiving member;
    a flexible back shield sheet covering the back face of said flexible printed circuit board; and
    a terminal member disposed on said flexible printed circuit board and which electrically connects said conductive sheet with said flexible back shield sheet.

2. An oximeter probe as claimed in claim 1, the oximeter probe further comprising:
    an auxiliary conductive and transparent shield sheet covering at least one of the windows of said conductive sheet, corresponding to the light receiving member.

3. An oximeter according to claim 2, wherein said conductive sheet and said auxiliary conductive and transparent shield sheet are integrally formed by a member which is conductive and transparent.

4. An oximeter probe as claimed in claim 3, wherein said flexible back shield sheet is formed by copper foil which is disposed on the back face of said flexible printed circuit board.

5. An oximeter probe as claimed in claim 1, wherein said flexible back shield sheet is formed by copper foil which is disposed on the back face of said flexible printed circuit board.

6. An oximeter probe as claimed in claim 2, wherein said flexible back shield sheet is formed by copper foil which is disposed on the back face of said flexible printed circuit board.

7. An oximeter probe as claimed in claim 1, further comprising:
    a heat sink layer disposed on an outer face of said flexible back shield sheet;
    a cover sheet adhered to an outer face of said heat sink layer;
    an auxiliary cover sheet covering an outer face of said conductive sheet, said auxiliary cover sheet being made of a material of which said cover sheet is also made; and
    a transparent sheet adhered to a surface of said auxiliary cover sheet.

8. An oximeter probe comprising:
    a flexible printed circuit board having a front face on which a light emitting member and a light receiving member are mounted and having a back face, said flexible printed circuit board being configured to be attached to a part of an object to measure an oxygen saturation of blood;
    a transparent conductive sheet covering the front face of said flexible printed circuit board on which the light emitting member and the light receiving member are mounted;
    a flexible back shield sheet covering the back face of said flexible printed circuit board; and
    a terminal member disposed on said flexible printed circuit board and which electrically connects said conductive sheet with said flexible back shield sheet.

9. An oximeter probe as claimed in claim 8, wherein said flexible back shield sheet is formed by copper foil which is disposed on the back face of said flexible printed circuit board.

* * * * *